US007358368B2

(12) United States Patent
Takahashi et al.

(10) Patent No.: US 7,358,368 B2
(45) Date of Patent: Apr. 15, 2008

(54) AZLACTONE COMPOUND AND METHOD FOR PREPARATION THEREOF

(75) Inventors: Daisuke Takahashi, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/980,298

(22) Filed: Nov. 4, 2004

(65) Prior Publication Data

US 2005/0137404 A1    Jun. 23, 2005

(30) Foreign Application Priority Data

Nov. 4, 2003 (JP) ............... 2003-374044

(51) Int. Cl.
C07D 263/18 (2006.01)
(52) U.S. Cl. ..................... 548/228; 548/237
(58) Field of Classification Search ............. 548/228, 548/237
See application file for complete search history.

(56) References Cited

U.S. PATENT DOCUMENTS

| 2,555,006 | A | * | 5/1951 | Rolfson et al. | ............... 560/41 |
| 2,569,801 | A | | 10/1951 | Cook et al. | |
| 5,948,785 | A | | 9/1999 | Akahoshi et al. | |
| 6,271,238 | B1 | | 8/2001 | Suzuki et al. | |
| 6,277,553 | B1 | * | 8/2001 | Taniguchi et al. | ........... 430/617 |
| 2004/0063936 | A1 | | 4/2004 | Sugiura et al. | |
| 2004/0230053 | A1 | | 11/2004 | Takahashi et al. | |
| 2005/0137404 | A1 | | 6/2005 | Takahashi et al. | |
| 2005/0209257 | A1 | | 9/2005 | Takahashi et al. | |

FOREIGN PATENT DOCUMENTS

| EP | 1 346 985 | 9/2003 |
| JP | 2003-104984 | 4/2003 |
| WO | WO 96/18644 | 6/1996 |
| WO | WO 96/33974 | 10/1996 |
| WO | WO 98/09949 | 3/1998 |
| WO | WO 98/24806 | 6/1998 |
| WO | WO 02/051815 | 7/2002 |
| WO | WO 03/106434 | 12/2003 |

OTHER PUBLICATIONS

Wikipedia, the free encyclopedia, on-line version.*
U.S. Appl. No. 11/181,985, filed Jul. 15, 2005, Takahashi et al.
K. Cucek et al, "Synthesis of Ethyl 3-(Benzoylamino)indole-2-Carboxylates Involving an Unexpected Migration of the Ethoxycarbonyl Group", Synlett, 1999, No. 1, pp. 120-122.
Francesca Clerici et al, "Conformationally Constrained Serine Analogues: Synthesis of New 2-Amino-3-hydroxynorbornanecarboxylic Acid Derivatives", J. Org. Chem., 2000, vol. 65, No. 19, pp. 6138-6141.
N. Leo Benoiton et al, "Amino-acid conjugates of the hapten 2-phenyl-4-ethoxymethylene-5(4H)-oxazolone", Int. J. Peptide Protein Res., vol. 45, 1995, pp. 266-271.

Ram S. Singh et al, "Synthesis of 4-(N,N-dimethylaminomethylene)-2-alkyl-2-oxazolin-5-ones via Vilsmeier Haack reagent and their reactions with various N- and O-nucleophiles", Indian Journal of Chemistry, vol. 39B, Sep. 2000, pp. 688-693.
Lucija Kralj et al, "Aminoacids in the Synthesis of Heterocyclic Systems. The Synthesis of Methyl 2-Acetylamino-3-dimethylaminopropenoate and 2-(N-Methyl-N-trifluoroacetyl)amino-3-dimethylaminopropenoate and their Application in the Synthesis of Heterocyclic Compounds", J. Heterocyclic Chem., vol. 34, Jan.-Feb. 1997, pp. 247-255.
Kumar K. Singh et al, "Unusual reactions of 2-aryl-4-(N,N-dimethylaminomethylene)-2-oxazolin-5-ones with O-nucleophiles: Synthesis of 2-aryl-4-hydroxymethylene-2-oxazolin-5-ones", Indian Journal of Chemistry, vol. 37B, No. 2, Feb. 1998, pp. 120-126.
John M. Bland et al, "Synthesis of (E)- and (Z)-Cyclopropyl-3-chloroalanine", J. Org. Chem., vol. 49, 1984, pp. 1634-1636.

(Continued)

Primary Examiner—Kamala A. Saeed
Assistant Examiner—Yong Chu
(74) Attorney, Agent, or Firm—Oblon, Spivak, McClelland, Maier & Neustadt, P.C.

(57) ABSTRACT

Compounds represented by formula (II):

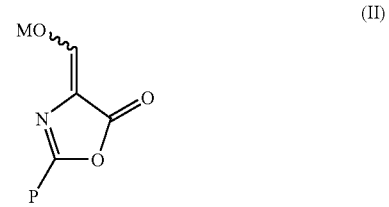

wherein M is a hydrogen atom, sodium, potassium, or lithium; P is a hydrogen atom, an alkyl group, and the like; and the wavy line indicates a cis form, a trans form, or a mixture thereof for the double bond to which it is attached, may be prepared by hydrolyzing a compound represented by formula (I), or a salt thereof:

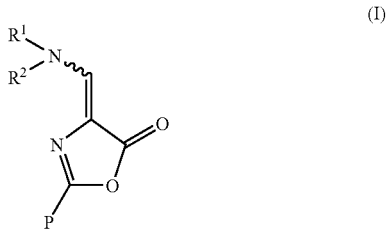

wherein $R^1$ and $R^2$ are the same or different and each is an alkyl group, or $R^1$ and $R^2$ together with the adjacent nitrogen atom may form an aliphatic heterocycle, and P and the wavy line are as defined above, in the presence of alkali metal hydroxide.

4 Claims, 2 Drawing Sheets

OTHER PUBLICATIONS

Lukas Wick et al, "Synthesis and Reactions of New 2-Substituted 5-Phenyl-6-oxa-4-azaspiro[2,4]-hepten-7-one Derivatives", *Tetrahedron*, vol. 51, No. 37, 1995, pp. 10219-10230.

Kazuyuki Ohmoto et al, "Development of Orally Active Nonpeptidic Inhibitors of Human Neutrophil Elastase", *J. Med. Chem.*, vol. 44, No. 8, 2001, pp. 1268-1285.

T. W. Greene et al, Protective Groups in Organic Synthesis, 2nd Edition, pp. 348-363, J. Wiley, 1991.

T.W. Greene et al, Protective Groups in Organic Synthesis, 3rd Edition, pp. 550-555, J. Wiley, 1999.

Database CHEMCATS Chemical Abstract Service, Columbus, Ohio, AN: 2002:3070446, PD: Mar. 15, 2005, ON: 2769, "Heterocyclic Compounds Catalog (milligram quantities)", Florida Center for Heterocyclic Compounds.

Database CHEMCATS Chemical Abstract Service, Columbus, Ohio, RN: 454218-11-1, EN: Entered STN: Sep. 23, 2002, CN: 5(4H)-Oxazolone, 4-(hydroxymethylene)-2-phenyl-, sodium salt (9CI) (CA INDEX NAME), Florida Center for Heterocyclic Compounds.

U.S. Appl. No. 10/980,298, filed Nov. 4, 2004, Takahashi et al.
U.S. Appl. No. 10/980,308, filed Nov. 4, 2004, Takahashi et al.
U.S. Appl. No. 11/010,346, filed Dec. 14, 2004, Takahashi et al.
U.S. Appl. No. 11/081,631, filed Mar. 17, 2005, Takahashi et al.
U.S. Appl. No. 11/417,233, filed May 4, 2006, Takahashi et al.

* cited by examiner

AZLACTONE COMPOUND AND METHOD FOR PREPARATION THEREOF

CROSS REFERENCES TO RELATED APPLICATIONS

This application claims priority to Japanese Patent Application No. 2003-374044 filed Nov. 4, 2003, the contents of which are hereby incorporated by reference in its entirety.

BACKGROUND OF THE INVENTION

1. Field of the Invention

The present invention relates to novel azlactone compounds which are useful as intermediates for pharmaceutical agents, agrichemicals, and the like. The present invention further relates to methods of preparing such azlactone compounds.

2. Discussion of the Background

Azlactone compounds represented by the formula (II):

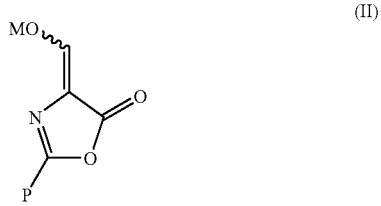

wherein P is a hydrogen atom, an alkyl group, an alkenyl group, an optionally substituted aryl group, an aralkyl group optionally having one or more substituent(s), or a haloalkyl group; and M is a hydrogen atom, sodium, potassium, or lithium, are useful as common starting materials for various heterocyclic derivatives such as pyrazoles, indoles, and the like, which are useful synthetic intermediates for pharmaceutical products, agrichemicals and the like, and various amino acid derivatives (see, e.g., *Synlett*, US, 1999, No. 1, pp. 120-122; and *The Journal of Organic Chemistry*, US, 2000, vol. 65, pp. 6138-6141), both of which are incorporated herein by reference in their entireties.

A known method for preparing azlactone compounds represented by formula (II) comprises reacting 4-ethoxymethylene-2-phenyl-5(4H)-oxazolone with an aqueous sodium hydroxide solution to give 4-hydroxymethylene-2-phenyl-5(4H)-oxazolone (*International Journal of Peptide and Protein Research, Netherlands*, 1995, vol. 45, pp. 266-271), which is incorporated by reference. However, a starting material compound in which the substituent at the 2-position of the azlactone ring is an aliphatic group (e.g., 4-ethoxymethylene-2-methyl-5(4H)-oxazolone, etc.) cannot be obtained in a high yield by this method, and the method is limited to compounds in which the substituent at the 2-position of the azlactone ring is an aromatic group such as a phenyl group and the like. Therefore, this method does not have high versatility.

A different method for the preparation of 4-hydroxymethylene-2-alkyl-2-oxazolin-5-one, which comprises reacting 4-(N,N-dimethylaminomethylene)-2-alkyl-2-oxazolin-5-one with sodium ethoxide in ethanol, is also known (*Indian Journal of Chemistry*, India, 2000, vol. 39B, pp. 688-693), which is incorporated herein by reference. However, when P is a methyl group or an ethyl group, this method also fails to provide an object compound in whihc M is a hydrogen atom. Although an azlactone compound in which P is a benzyl group and the like and M is a hydrogen atom can be obtained, a by-product such as a ring-opened product and the like occurs, and the method is not entirely satisfactory.

Thus, there remains a need for novel compounds of formula (II) described above. There also remains a need for improved methods for preparing compounds according to formula (II):

SUMMARY OF THE INVENTION

Accordingly, it is one object of the present invention to provide novel azlactone compounds.

It is another object of the present invention to provide novel azlactone compounds, which is useful as an intermediate for pharmaceutical products and the like.

It is another object of the present invention to provide novel methods for preparing such azlactone compounds.

These and other objects, which will become apparent during the following detailed description, have been achieved by the inventors' discovery that by reacting an azlactone compound represented by the formula (I) set out below, which is a known compound, with an aqueous solution of alkali metal hydroxide, the azlactone compound represented by formula (II) can be surprisingly obtained in a high yield under mild conditions.

Furthermore, the present inventors have also succeeded in synthesizing a novel azlactone compound represented by the formula (II') to be mentioned later by adapting this method.

Thus, the present invention provides the following:

(1) A method of preparing a compound represented by formula (II):

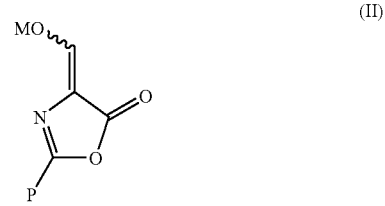

wherein M is a hydrogen atom, sodium, potassium, or lithium; P is a hydrogen atom, an alkyl group, an alkenyl group, an aryl group optionally having one or more substituents, an aralkyl group optionally having one or more substituents, or a haloalkyl group; and a wavy line indicates a cis form, a trans form or a mixture thereof for the carbon-carbon double bond to which it is attached, which comprises hydrolyzing a compound represented by formula (I):

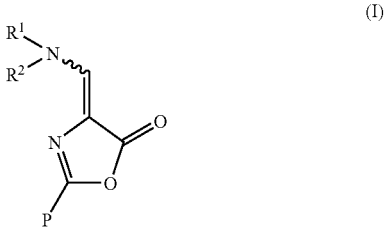

wherein R[1] and R[2] are the same or different and each is an alkyl group, or may be bonded to each other to form an aliphatic heterocycle together with the adjacent nitrogen atom; and P and a wavy line are as defined above (hereinafter to be also referred to as compound (I)), or a salt thereof, in the presence of alkali metal hydroxide, to obtain the compound of formula (II).

(2) The method of the above-mentioned (1), wherein P is a methyl group, an ethyl group, a benzyl group, a p-tolyl group, or a p-chlorophenyl group.

(3) The method of the above-mentioned (1) or (2), wherein M is sodium or potassium.

(4) The method of any of the above-mentioned (1) to (3), which is performed in a solvent other than alcohol solvents.

(5) The method of the above-mentioned (1), wherein said alkali metal hydroxide comprises at least one alkali metal hydroxide selected from the group consisting of sodium hydroxide, potassium hydroxide, lithium hydroxide, and mixtures thereof.

(6) The method of the above-mentioned (1) to (3), wherein said alkali metal hydroxide comprises at least one alkali metal hydroxide selected from the group consisting of sodium hydroxide, potassium hydroxide, and mixtures thereof.

(7) A compound represented by the formula (II'):

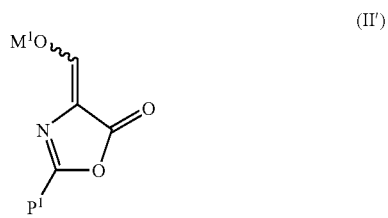

wherein $P^1$ is an alkyl group, an alkenyl group, an aryl group having one or more substituents, an aralkyl group optionally having one or more substituents, or a haloalkyl group; $M^1$ is sodium, potassium, or lithium, and a wavy line indicates a cis form, a trans form, or a mixture thereof for the carbon-carbon double bond to which it is attached.

(8) The compound of the above-mentioned (7), wherein $P^1$ is a methyl group, an ethyl group, a benzyl group, a p-tolyl group, or a p-chlorophenyl group.

(9) The compound of the above-mentioned (7) or (8), wherein $M^1$ is sodium or potassium.

(10) The compound of any of the above-mentioned (7) to (9), which is an anhydrous crystal.

Thus, the present invention provides a method of advantageously preparing compounds represented by the formula (II), which are useful synthetic intermediates for pharmaceutical products, agrichemicals, and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
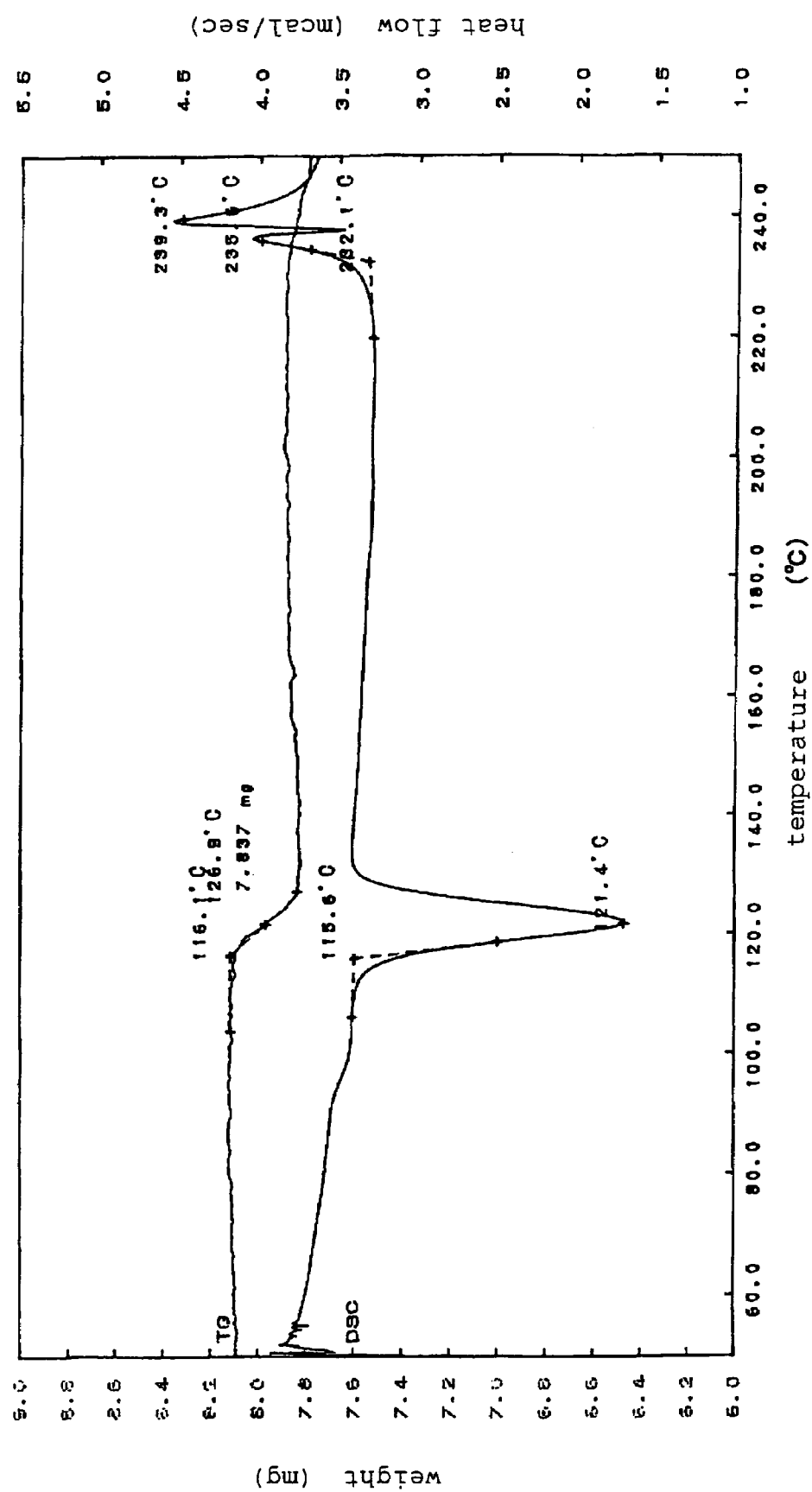
FIG. 1 is a chart showing the results of thermal analysis (DSC and TG) of the compound of Example 2.

Thus, in a first embodiment, the present invention provides novel methods of preparing a compound represented by formula (II):

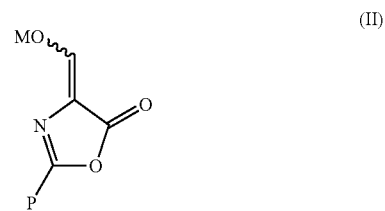

wherein M is a hydrogen atom, sodium, potassium, or lithium; P is a hydrogen atom, an alkyl group, an alkenyl group, an aryl group optionally having one or more substituents, an aralkyl group optionally having one or more substituents, or a haloalkyl group; and a wavy line indicates a cis form, a trans form or a mixture thereof for the carbon-carbon double bond to which it is attached, which comprises hydrolyzing a compound represented by formula (I):

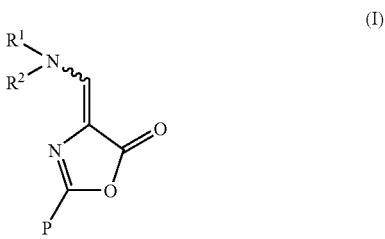

wherein R[1] and R[2] are the same or different and each is an alkyl group, or may be bonded to each other to form an aliphatic heterocycle together with the adjacent nitrogen atom; and P and a wavy line are as defined above (hereinafter to be also referred to as compound (I)), or a salt thereof, in the presence of alkali metal hydroxide, to obtain the compound of formula (II).

In addition, in a second embodiment, the present invention provides novel compounds represented by the formula (II'):

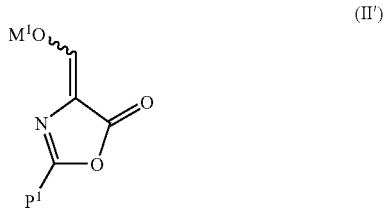

wherein $P^1$ is an alkyl group, an alkenyl group, an aryl group having one or more substituents, an aralkyl group optionally having one or more substituents, or a haloalkyl group; $M^1$ is sodium, potassium, or lithium, and a wavy line indicates a cis form, a trans form, or a mixture thereof for the carbon-carbon double bond to which it is attached.

The definitions of symbols used in the present invention are as follows.

The "alkyl group" for P, $P^1$, $R^1$ or $R^2$ is a linear or branched chain alkyl group preferably having 1 to 20, more preferably 1 to 7, carbon atoms, such as methyl group, ethyl group, n-propyl group, isopropyl group, n-butyl group, isobutyl group, sec-butyl group, tert-butyl group, lauryl group and the like. Of these, methyl group and ethyl group are preferable.

The "aryl group optionally having one or more substituents" for P is an aryl group preferably having 6 to 20, more preferably 6 to 8, carbon atoms. The aryl group is optionally substituted by one or more of the following substituents. As used herein, the substituent includes, for example, a nitro group, a linear or branched chain alkoxy group (carbon number: 1-6, e.g.: methoxy group), halogen atom (e.g.: chlorine atom, fluorine atom, and the like), a linear or branched chain alkyl group (preferable carbon number: 1-4, e.g.: methyl group, ethyl group, propyl group, tert-butyl, and the like), and the like. Specific examples of the aryl group optionally having one or more substituents include phenyl group, o-, m-, or p-nitrophenyl group, o-, m-, or p-methoxyphenyl group, o-, m-, or p-chlorophenyl group, o-, m-, or p-fluorophenyl group, o-, m-, or p-tolyl group, and the like, with preference given to phenyl group, p-chlorophenyl group, p-tolyl group, and the like.

The "aryl group having one or more substituents" for $P^1$ is an aryl group preferably having 6 to 20, more preferably 6 to 8, carbon atoms and having one or more of the above-mentioned substituents. Specific examples of the aryl group having one or more substituents include o-, m-, or p-nitrophenyl group, o-, m-, or p-methoxyphenyl group, o-, m-, or p-chlorophenyl group, o-, m-, or p-fluorophenyl group, o-, m-, or p-tolyl group, and the like, with preference given to p-chlorophenyl group and p-tolyl group.

The "alkenyl group" for P or $P^1$ is a linear or branched chain alkenyl group preferably having 2 to 20, more preferably 2 to 7, carbon atoms, and includes, for example, vinyl group, allyl group, homoallyl group, oleyl group, β-styryl group, and the like, with preference given to vinyl group, allyl group, and β-styryl group.

The "aralkyl group" of the "aralkyl group optionally having one or more substituents" for P or $P^1$ is an aralkyl group wherein the aryl moiety is an aryl group preferably having 6 to 12, more preferably 6 to 8, carbon atoms, and the alkylene moiety is a linear or branched chain alkylene group preferably having 1 to 6, more preferably 1 to 3, carbon atoms. The aralkyl group is optionally substituted by one or more of the following substituents. As used herein, the substituent includes, for example, a nitro group, a linear or branched chain alkoxy group (carbon number: 1-6, e.g.: methoxy group), halogen atom (e.g.: chlorine atom, fluorine atom, and the like), a linear or branched chain alkyl group (preferable carbon number: 1-4, e.g.: methyl group, ethyl group, propyl group, and the like), and the like. As the aralkyl group optionally having substituent(s), a benzyl group is preferable.

The "haloalkyl group" for P or $P^1$ is a straight chain or branched chain alkyl group preferably having 1 to 5, more preferably 1 to 3, carbon atoms, which is substituted by one or more halogen atoms (fluorine atom, chlorine atom, bromine atom, iodine atom), such as trifluoromethyl group, trichloromethyl group, chloromethyl group, and the like, with preference given to trifluoromethyl group and chloromethyl group.

The "aliphatic heterocycle" formed by $R^1$ and $R^2$ together with the adjacent nitrogen atom is a 5- or 6-membered aliphatic heterocycle containing a carbon atom and at least one nitrogen atom, and besides these, optionally containing 1 to 3 hetero atoms selected from oxygen atom, sulfur atom, and nitrogen atom, such as pyrrolidine, piperidine, morpholine, thiomorpholine, piperazine, and the like.

P is preferably an alkyl group or an aralkyl group optionally having one or more substituents, and methyl group, ethyl group, and benzyl group are more preferable. As the alkyl group for $R^1$ or $R^2$, methyl group or ethyl group is preferable, and as the aliphatic heterocycle optionally formed together with the adjacent nitrogen atom, morpholine or piperidine is preferable.

M is preferably sodium, potassium, or lithium, and sodium or potassium is more preferable.

$M^1$ is preferably sodium, potassium, or lithium, and sodium or potassium is more preferable.

The preparation method of the present invention produces compound (II) by hydrolyzing compound (I) in water or a mixed solvent of water and an organic solvent in the presence of alkali metal hydroxide. To be specific, for example, alkali metal hydroxide, preferably an aqueous solution thereof, is added to compound (I) in a solvent. The order of addition may be reversed or the liquids may be combined simultaneously.

The preparation method of the present invention is advantageous, because compound (II) can be synthesized in a high yield under mild conditions by the use of alkali metal hydroxide.

In addition, the present invention is applicable to a wide range of use since, even when P of compound (II) to be prepared is methyl or ethyl, it can be isolated as a stable salt when M is an alkali metal such as sodium and the like.

As the alkali metal hydroxide to be used in the present method, sodium hydroxide, potassium hydroxide, lithium hydroxide, and the like can be mentioned, with preference given to sodium hydroxide. The alkali metal hydroxide may be used in the form of a solid but is preferably used in the form of an aqueous solution. In this case, the concentration is suitably within the range of 0.1N to 8N.

The amount of the alkali metal hydroxide to be used is generally 0.9-1.8 equivalents, preferably 1-1.3 equivalents, relative to number of moles of compound (I).

As the solvent to be used in the present invention, any solvent can be used as long as it does not inhibit the reaction, and, for example, water, acetates (e.g., ethyl acetate, isopropyl acetate, isobutyl acetate, n-butyl acetate, etc.), acetonitrile, tetrahydrofuran (THF), N,N-dimethylformamide, acetone, and the like can be mentioned. These may be used in combination of two or more kinds thereof. The use of a mixed solvent of water and an organic solvent miscible with water, such as acetonitrile, acetone, and the like, is more preferable, and a mixed solvent of acetonitrile and water is particularly preferable. The amount of solvent to be used is generally 3- to 50-fold weight, preferably 5- to 20-fold weight, relative to the weight of compound (I). When an aqueous solution of alkali metal hydroxide is to be used, the amount of water is included in the amount of solvent.

The use of an alcohol solvent (e.g., ethanol, isopropyl alcohol, n-butanol, etc.) is not preferred, because side reactions such as ring opening of azlactone ring of compound (I) and the like tend to occur.

The reaction is conducted at a temperature in the range of generally from 0° C. to the refluxing temperature of the solvent to be used (preferably 0° C. to 30° C.). The reaction is typically completed, at the above-mentioned temperature range, in a time period of generally from 60 min to one night (preferably 2 hr to 20 hr).

After the completion of the reaction, compound (II) is present in the form of an alkali metal salt (M=alkali metal). Therefore, when the free form (M=hydrogen atom) of compound (II) is to be isolated, an acid (e.g., hydrochloric acid, sulfuric acid, etc.) is added to the reaction mixture to adjust the pH to a value of 3 to 5, and the free form of compound (II) can be isolated by any suitable general isolation and purification method, such as concentration, crystallization by adding a crystallization solvent (e.g., ethers (e.g.: diethyl ether, THF, and the like), acetone, acetonitrile, a hydrocarbon solvent (e.g., toluene, benzene, hexane, heptane, and the like), a halogen solvent (e.g., dichloromethane, dichloroethane, and the like), water or a mixed solvent thereof, and the like) or silica gel column chromatography of the reaction mixture, but the method is not limited to these.

For isolation in the form of an alkali metal salt, an alkali metal salt of compound (II) can be isolated by any suitable general isolation and purification method, such as concentration of the reaction mixture or crystallization from the reaction mixture by the addition of the above-mentioned crystallization solvent, but the method is not limited to these.

Moreover, an alkali metal salt of compound (II) easily becomes a hydrate, and therefore, it is preferable to obtain the compound as an anhydrous crystal by high temperature drying, high temperature slurry washing in an organic solvent, and the like.

The compounds of formula (I), which are used as starting materials, can be prepared by a known method.

For example, as described in Reference Examples 1-3, below, the compounds of formula (I) can be prepared by reacting N-acylglycine represented by the formula: PC(=O)NHCH$_2$COOH wherein P is as defined above, with formamide represented by the formula: R$^1$R$^2$NCHO wherein each symbol is as defined above and phosphorus oxychloride (see, *Ind. J. Chem.*, vol. 39B, pp. 688-693 (2000), which is incorporated herein by reference).

In addition, as described in Reference Example 4, below, the compounds of formula (I) can be prepared by reacting N-acylglycine represented by the formula: PC(=O)NHCH$_2$COOH wherein P is as defined above with formamide dimethylacetal represented by the formula: R$_1$R$^2$NCH(OMe)$_2$ wherein each symbol is as defined above in the presence of N,N'-dicyclohexylcarbodiimide (see, *J. Heterocyclic Chem.*, vol. 34, p. 247 (1997), which is incorporated herein by reference).

The compounds of formula (II) obtained by the present invention can be converted to an indole derivative, a pyrazole derivative, or an amino acid derivative by a method described in, for example, the above-mentioned *Synlett*, US, 1999, vol. 1, pp. 120-122; and *The Journal of Organic Chemistry*, US, 2000, vol. 65, pp. 6138-6141, both of which are incorporated herein by reference.

The compounds of formula (II'), which are a subset or subgenus of the compounds of formula (II) to be prepared in the present invention are novel compounds and are useful as novel synthetic intermediates for preparing pharmaceutical products, agrichemicals and the like.

Other features of the invention will become apparent in the course of the following descriptions of exemplary embodiments which are given for illustration of the invention and are not intended to be limiting thereof.

EXAMPLES

Reference Example 1

4-(N,N-dimethylaminomethylene)-2-methyl-5-oxazolinone

To N-acetylglycine (20.0 g, 171 mmol) were added phosphorus oxychloride (67.0 g, 437 mmol) and N,N-dimethylformamide (33.0 g, 451 mmol) in an ice bath, and the mixture was stirred at 45° C. for 1.5 hr. The reaction mixture was concentrated under reduced pressure and added dropwise to 28% aqueous ammonia (150 ml), while maintaining the temperature at not more than 10° C. The mixture was stirred in an ice bath for 1 hr, and the precipitate was collected by filtration. The obtained crystals were washed successively with water and ethanol and dried to give the title compound as crystals (20.2 g, 131 mmol).

$^1$H-NMR (CDCl$_3$) δ: 2.21 (3H, s), 3.18 (3H, m), 3.47 (3H, s), 6.96 (1H, s). MS (ESI) m/z [MH]+155.2

Reference Example 2

2-benzyl-4-(N,N-dimethylaminomethylene)-5-oxazolinone

To phenaceturic acid (10.0 g, 51.8 mmol) were added chloroform (30.0 ml), phosphorus oxychloride (20.0 g, 130 mmol), and N,N-dimethylformamide (10.0 g, 137 mmol) in an ice bath, and the mixture was stirred at 45° C. for 1.5 hr. The reaction mixture was concentrated under reduced pressure and added dropwise to 28% aqueous ammonia (65 ml), while maintaining the temperature at not more than 10° C. The mixture was extracted with chloroform, and the organic layer was washed with water and saturated brine and concentrated to dryness. The concentrate was washed with isopropyl alcohol, and the precipitate was collected by filtration, washed with isopropyl alcohol, and dried to give the title compound as crystals (9.90 g, 43.3 mmol).

$^1$H-NMR (CDCl$_3$) δ: 3.17 (3H, s), 3.48 (3H, m), 3.83 (2H, s), 6.97 (1H, s), 7.23-7.36 (5H, m) MS (ESI) m/z [MH]+ 231.5

Reference Example 3

2-methyl-4-(morpholinomethylene)-5-oxazolinone

To N-acetylglycine (0.50 g, 4.27 mmol) were added phosphorus oxychloride (995 μl, 10.7 mmol) and N-formylmorpholine (1.23 g, 10.7 mmol) in an ice bath, and the mixture was stirred at 45° C. for 1.5 hr. The reaction mixture was concentrated under reduced pressure and added dropwise to 28% aqueous ammonia (5 ml) and water (5 ml), while maintaining the temperature at not more than 10° C. The reaction mixture was stirred in an ice bath for 1 hr, and the precipitate was collected by filtration. The obtained crystals were washed successively with water and ethanol and dried to give the title compound as crystals (0.52 g, 2.65 mmol).

$^1$H-NMR (CDCl$_3$) δ: 2.21 (3H, s), 3.47 (2H, br), 3.79 (4H, t, J=4.8 Hz), 4.27 (2H, s), 6.92 (1H, s) MS (ESI) m/z [MH]+196.9

Reference Example 4

2-benzyl-4-(N,N-dimethylaminomethylene)-5-oxazolinone

To phenaceturic acid (1.00 g, 5.18 mmol) were added toluene (10.0 ml) and N,N'-dicyclohexylcarbodiimide (1.07 g, 5.19 mmol), and the mixture was stirred at room temperature overnight. The precipitate was removed by filtration, and N,N-dimethylformamide dimethylacetal (0.68 g, 5.71 mmol) was added. The mixture was stirred overnight. The reaction mixture was washed with saturated brine and concentrated to dryness. Isopropyl alcohol was added to the concentrate to allow crystallization, and the precipitate was collected by filtration, washed with isopropyl alcohol, and vacuum dried to give the title compound as crystals (0.78 g, 3.39 mmol).

Example 1

4-hydroxymethylene-2-methyl-5-oxazolinone Sodium Salt．anhydride

To a solution (50 ml) of 4-(N,N-dimethylaminomethylene)-2-methyl-5-oxazolinone (4.00 g, 26.0 mmol) in acetonitrile was added 2N aqueous sodium hydroxide solution (15 ml, 30.0 mmol) under ice-cooling, and the mixture was stirred overnight. Water was evaporated, and acetonitrile (30 ml) was added, and the mixture was stirred at 61° C. for 71 hr. The precipitate was collected by filtration, washed with acetonitrile, and vacuum dried at 80° C. to give the title compound as white crystals (3.65 g, 24.5 mmol).
$^1$H-NMR (DMSO-$d_6$) δ: 2.00 (3H, s), 8.67 (3H, s) MS (API-ES) m/z [MH]+126.1

Example 2

2-benzyl-4-hydroxymethylene-5-oxazolinone Sodium Salt.1 hydrate

To a solution (120 ml) of 2-benzyl-4-(N,N-dimethylaminomethylene)-5-oxazolinone (10.8 g, 46.9 mmol) in acetonitrile was added 1N aqueous sodium hydroxide solution (53 ml, 53.0 mmol) under ice-cooling, and the mixture was stirred overnight. Acetonitrile was evaporated to allow crystallization under ice-cooling. The precipitate was collected by filtration and vacuum dried to give the title compound as white crystals (5.99 g, 26.6 mmol). Differential scanning calorie (DSC) and thermal gravity (TG) were measured using a thermal analyzer (Rigaku Corporation, TAS-200). As a result, an endothermic peak appeared at 121.4° C., and weight decrease was observed at 116.1-126.9° C. The chart is shown in FIG. 1.
$^1$H-NMR (DMSO-$d_6$) δ: 3.66 (2H, s), 7.22-7.32 (5H, m), 8.71 (1H, s) MS (ESI) m/z [MH]−202.1

Example 3

2-benzyl-4-hydroxymethylene-5-oxazolinone Sodium Salt.anhydride

Figure 2:
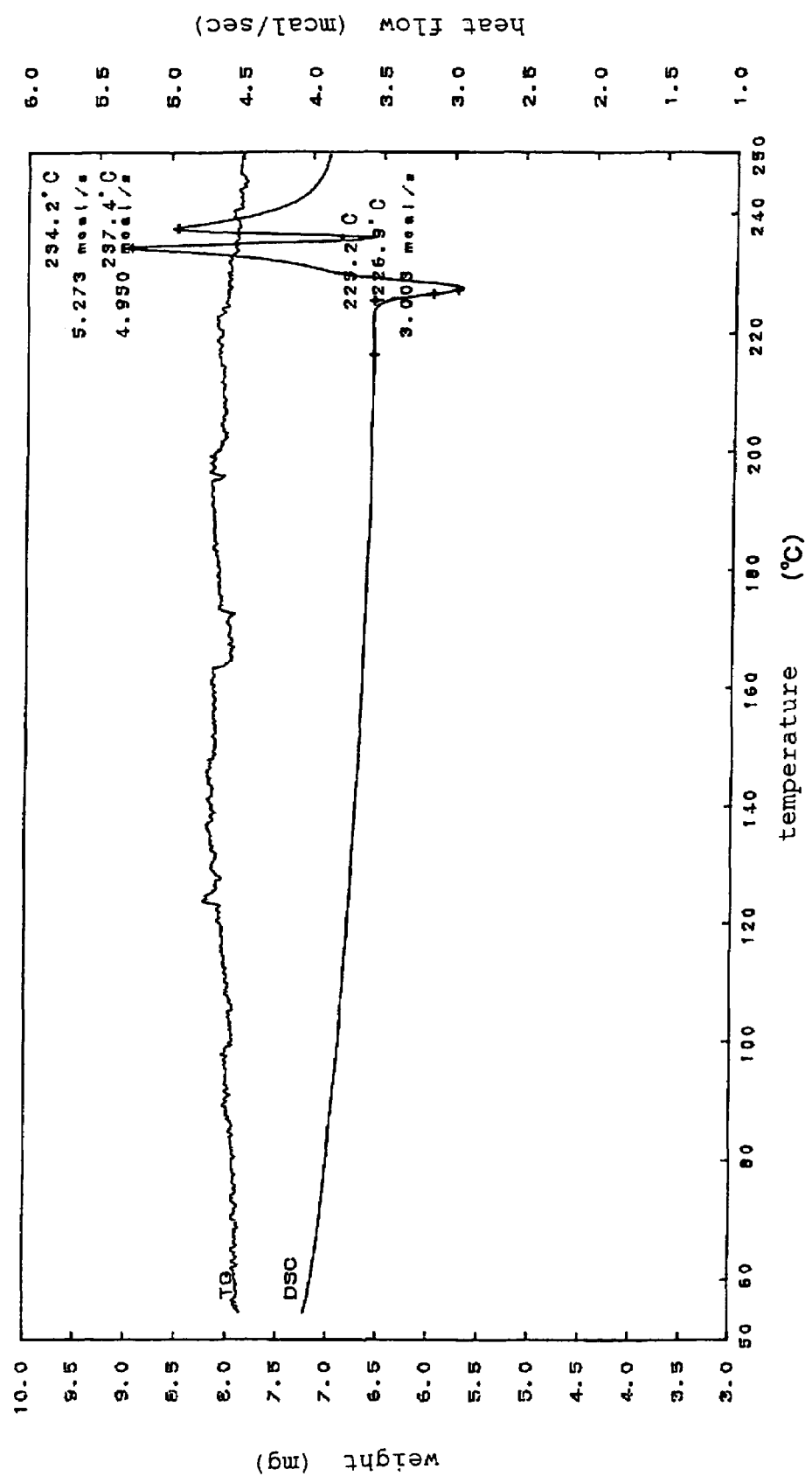
FIG. 2 is a chart showing the results of thermal analysis (DSC and TG) of the compound of Example 3.

To a solution (10 ml) of 2-benzyl-4-(N,N-dimethylaminomethylene)-5-oxazolinone (1.00 g, 4.34 mmol) in acetonitrile was added 1N aqueous sodium hydroxide solution (5 ml, 5.00 mmol) under ice-cooling, and the mixture was stirred overnight. The reaction mixture was concentrated to dryness. Acetonitrile (5 ml) was added, and the precipitate was collected by filtration and dried at 100° C. for 2 hr to give the title compound as white crystals (0.90 g, 4.00 mmol). DSC and TG were measured using a thermal analyzer. As a result, an endothermic peak and clear weight change were not observed up to 220° C. The chart is shown in FIG. 2.
$^1$H-NMR (DMSO-$d_6$) δ: 3.66 (2H, s), 7.22-7.32 (5H, m), 8.71 (1H, s) MS (ESI) m/z [MH]−202.1

Example 4

2-benzyl-4-hydroxymethylene-5-oxazolinone

To a solution (15 ml) of 4-N,N'-dimethylaminomethylene-2-benzyl-5-oxazoline (350 mg, 6.65 mmol) in acetonitrile was added 2N aqueous sodium hydroxide solution (0.92 ml) under ice-cooling, and the mixture was stirred overnight at room temperature. The reaction mixture was concentrated to evaporate acetonitrile. The mixture was washed with ethyl acetate (5 ml), and the aqueous layer was neutralized with 1N hydrochloric acid to pH 4 under ice-cooling. The precipitate was collected by filtration, washed with water and vacuum dried to give the title compound as crystals (1.03 g, 5.07 mmol).
$^1$H-NMR (DMSO-$d_6$) δ: 3.92 (2H, s), 7.29-7.38 (5H, m), 7.68 (1H, s) MS (ESI) m/z [MH]−202.3

Example 5

2-tolyl-4-hydroxymethylene-5-oxazolinone Sodium Salt

In the same manner as in Example 1, except that 4-(N,N-dimethylaminomethylene)-2-tolyl-5-oxazolinone was used instead of 4-(N,N-dimethylaminomethylene)-2-methyl-5-oxazolinone, the title compound was obtained.
$^1$H-NMR (DMSO-$d_6$) δ: 2.32 (3H, s), 7.21 (2H, d, J=8.2 Hz), 7.63 (2H, d, J= 8.2 Hz), 8.88 (1H, s)

Comparative Example 1

To a solution of 4-N,N-dimethylaminomethylene-2-benzyl-5-oxazolinone (242 mg, 1.05 mmol) in ethanol (8 ml) was added sodium hydroxide (50 mg, 1.25 mmol) under ice-cooling, and the mixture was stirred at room temperature for 2 hr. The solvent was evaporated, water was added, and the mixture was neutralized with 2N hydrochloric acid. After the completion of the reaction and after neutralization, the mixture was subjected to HPLC, MS analyses to find a ring open form, ethyl 2-phenylacetylamino-3-N,N-dimethylaminopropionate.

Since the compound of formula (II) obtained by the present method can be a synthetic starting material for indole derivatives and amino acid derivatives having biological activity (see, *Synlett*, US, 1999, vol. 1, pp. 120-122; and *The Journal of Organic Chemistry*, US, 2000, vol. 65, pp. 6138-6141), it is useful as a synthetic intermediate for pharmaceutical agents, agrichemicals, and the like.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A compound represented by the formula (II'):

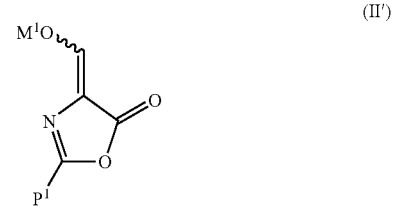

(II')

wherein:
P$^1$ is a methyl group or a benzyl group;
M$^1$ is sodium or potassium; and
a wavy line indicates a cis form, a trans form, or a mixture thereof for the carbon-carbon double bond to which it is attached,
wherein said compound is an anhydrous crystal.

2. The compound of claim 1, wherein P$^1$ is a methyl group.

3. The compound of claim 1, wherein M$^1$ is sodium.

4. The compound of claim 3, wherein P$^3$ is a methyl group.

* * * * *